United States Patent [19]

Wall et al.

[11] Patent Number: 5,278,072
[45] Date of Patent: Jan. 11, 1994

[54] CALIBRATION SYSTEM AND HOUSING

[75] Inventors: Roxanne E. Wall, Newport Beach; Thomas P. Maxwell, Santa Ana, both of Calif.

[73] Assignee: Minnesota Mining and Manufacturing Company, St. Paul, Minn.

[21] Appl. No.: 849,753

[22] Filed: Mar. 12, 1992

Related U.S. Application Data

[60] Continuation-in-part of Ser. No. 747,533, Aug. 20, 1991, Pat. No. 5,171,029, which is a division of Ser. No. 514,704, Apr. 26, 1990, Pat. No. 5,057,278.

[51] Int. Cl.$^5$ ............................................ G01N 21/00
[52] U.S. Cl. ............................................ 436/8; 436/11; 422/68.1; 422/81; 422/102; 422/103; 128/DIG. 12; 128/DIG. 13
[58] Field of Search ........................ 436/8, 11 422/68.1, 81, 102, 103; 128/DIG. 12, 13

[56] References Cited

U.S. PATENT DOCUMENTS

| | | | |
|---|---|---|---|
| 2,002,862 | 5/1935 | Moran | 417/476 |
| 2,403,572 | 7/1946 | Wittenberg | 418/45 |
| 2,503,376 | 4/1950 | Burgess | 137/122 |
| 2,579,203 | 12/1951 | Putney | 261/3 |
| 2,585,440 | 2/1952 | Collins | 55/257.1 |
| 2,628,825 | 2/1953 | Kantor et al. | 261/140.1 |
| 3,334,657 | 8/1967 | Smith et al. | 137/888 |
| 3,874,850 | 4/1975 | Sorensen et al. | 436/50 |
| 3,884,640 | 5/1975 | Lock et al. | 422/82.03 |
| 4,119,406 | 10/1978 | Clemens | 422/81 |
| 4,266,941 | 5/1981 | Sullivan | 436/68 |
| 4,285,703 | 8/1981 | Alexander | 55/228 |
| 4,401,547 | 8/1983 | Schinkmann et al. | 204/415 |
| 4,424,276 | 1/1984 | Clark et al. | 435/50 |
| 4,443,407 | 4/1984 | Weinberg et al. | 422/82.04 |
| 4,516,580 | 5/1985 | Polanyi | 128/632 |
| 4,537,561 | 8/1985 | Xanthopoulos | 417/477 |
| 4,559,040 | 12/1985 | Horres et al. | 604/153 |
| 4,573,884 | 3/1986 | Troutner | 417/374 |
| 4,604,263 | 8/1986 | Smernoff | 422/50 |
| 4,635,467 | 1/1987 | Hoffa et al. | 73/16 |
| 4,640,820 | 2/1987 | Cooper | 422/68 |
| 4,668,634 | 5/1987 | Iwaski et al. | 436/68 |
| 4,758,228 | 7/1988 | Williams | 604/153 |
| 4,764,315 | 8/1988 | Brusa | 261/140.1 |
| 4,798,590 | 1/1989 | O'Leary et al. | 604/153 |
| 4,830,013 | 5/1989 | Maxwell | 128/637 |
| 4,844,871 | 7/1989 | Polaschegg | 422/81 |
| 5,057,278 | 10/1991 | Maxwell et al. | 422/68.1 |
| 5,094,820 | 3/1992 | Maxwell et al. | 422/82.12 |

OTHER PUBLICATIONS

Filtering Functions-Filtration-Demisting-Humidification-Separation—a five page Foamex product brochure from Rogers Foam Morris Company.
McMaster-Carr Supply Company Catalog 97, p. 143 (1991).
Shiley 100A Blood Oxgenator product literature, p. 32.
Viking Technology, Inc. product literature, pp. 1-5.
Souknanou et al., Webster's II New Riverside University Dictionary; 1984, p. 341.
"Corrosion-Resistant Ventilation", *McMaster-Carr Supply Company*, Catalog 97, p. 143.

*Primary Examiner*—Lyle A. Alexander
*Attorney, Agent, or Firm*—Gary L. Griswold; Walter N. Kirn; Dale E. Hulse

[57] ABSTRACT

A calibration system comprising a sensor cassette including at least one sensor to be calibrated and a housing having a liquid passage including a chamber. The housing is coupled to the sensor cassette to place the liquid passage in fluid communication with the sensor cassette. The housing has a gas injection passage through which a gas can be injected into the liquid passage to mix with a calibration liquid in the housing. A gas vent vents the gas from the housing. Porous media is provided in the chamber. The gas and calibration liquid pass through the porous media, and the porous media assists in rapid mixing of the gas and the calibration liquid.

29 Claims, 2 Drawing Sheets

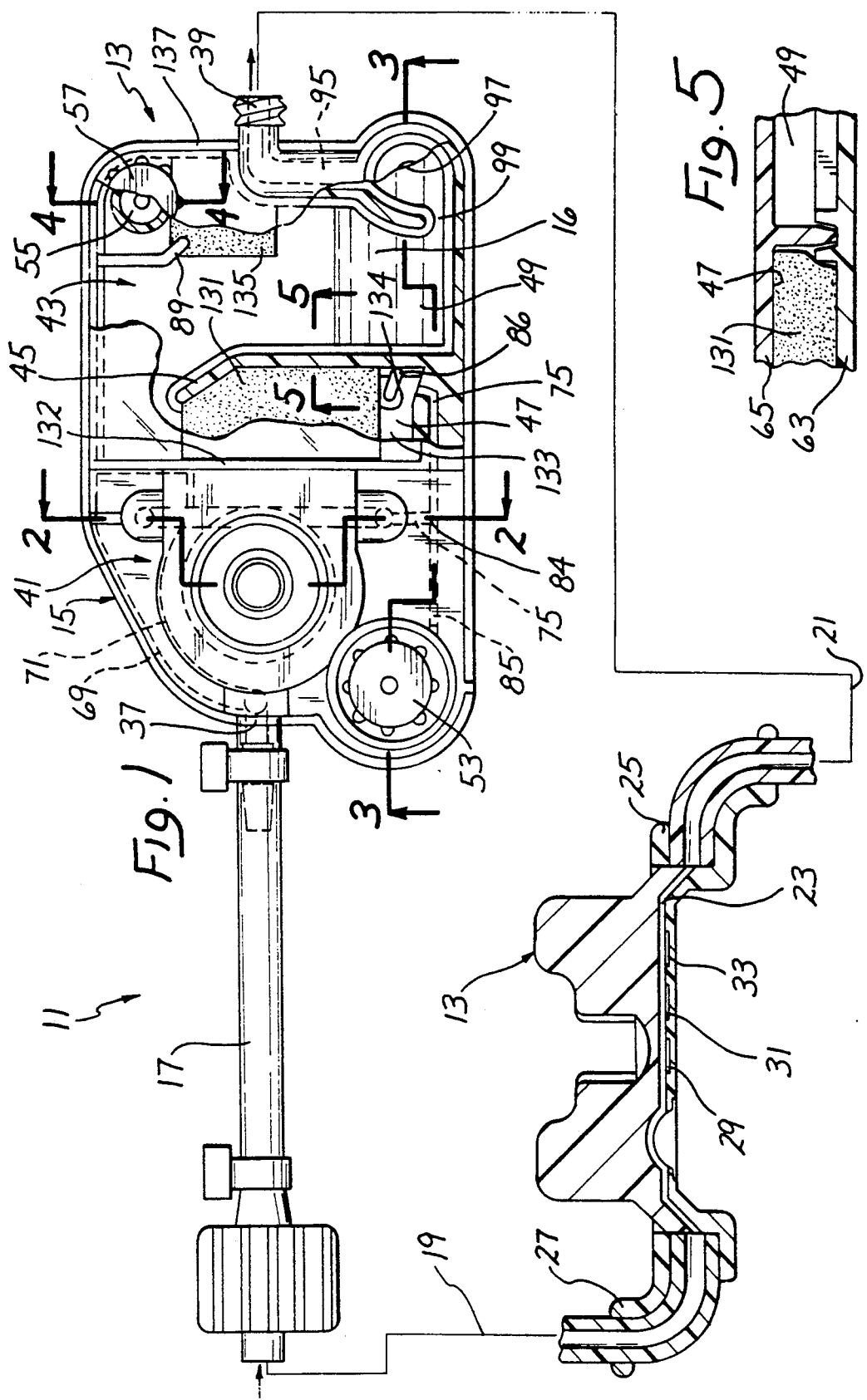

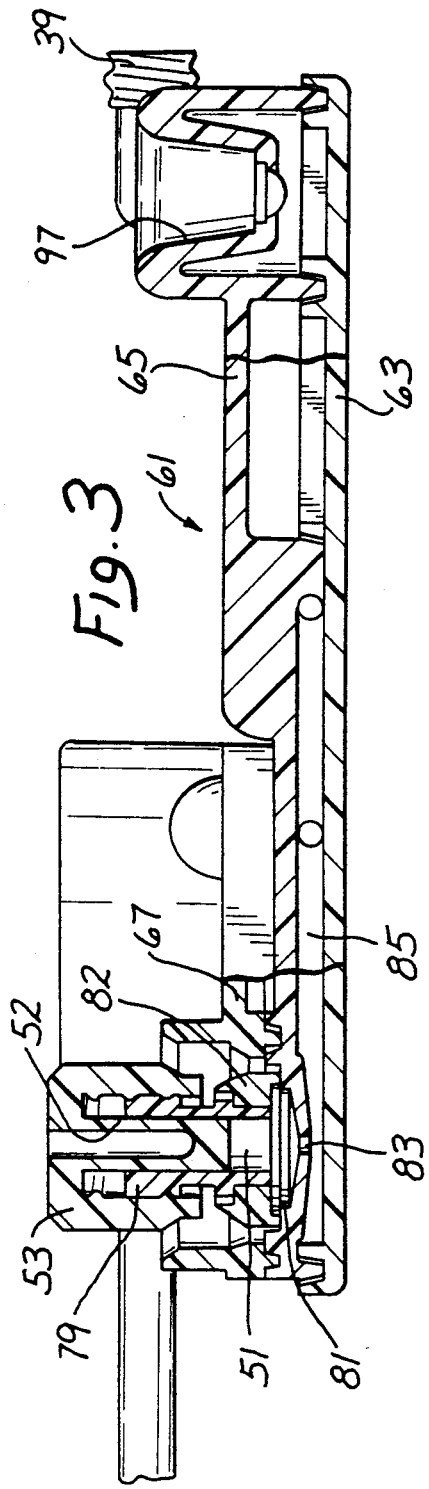
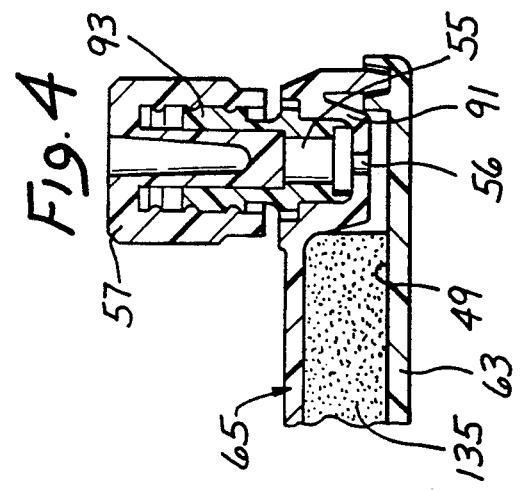
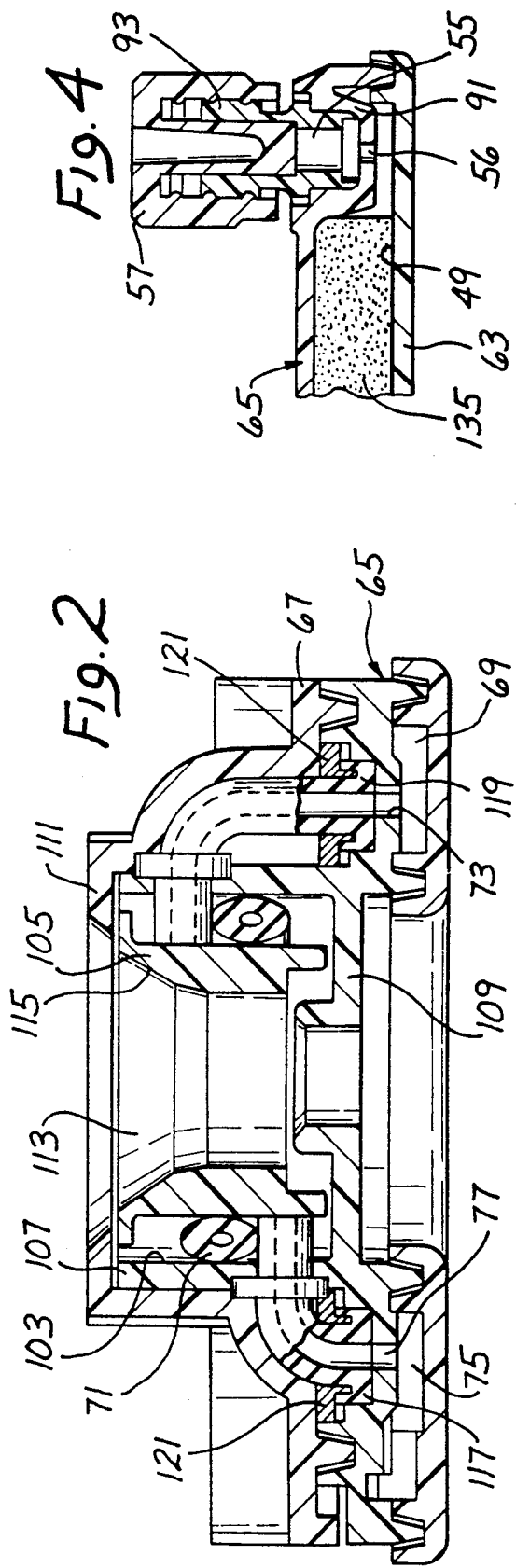

CALIBRATION SYSTEM AND HOUSING

CROSS REFERENCE TO RELATED APPLICATIONS

This application is a continuation-in-part of application Ser. No. 747,533 filed on Aug. 20, 1991 now U.S. Pat. No. 5,171,029 which is a division of application Ser. No. 514,704 filed on Apr. 26, 1990 now U.S. Pat. No. 5,057,278.

BACKGROUND OF THE INVENTION

It is often necessary or desirable to monitor various parameters of blood and to obtain quantitative data concerning such parameters in real time. One way to accomplish this is to flow blood through a flow-through housing past sensors which provide signals representative of the parameters of interest. For example, Cooper U.S. Pat. No. 4,640,820 shows a flow-through housing with fluorescent sensors which respond to the partial pressure of oxygen, the partial pressure of carbon dioxide and the pH of blood which has passed through the flow-through housing.

Prior to using the flow-through housing, the sensors must be calibrated. One calibration technique, which is used for the sensors of the Cooper patent, is to attach the sensor carrier to a calibration housing containing calibration liquid. This places the sensors in communication with a relatively large cross-sectional area passage. The gas or gases of interest are then bubbled through the calibration liquid. A similar technique is utilized to calibrate the sensors shown in Maxwell U.S. Pat. No. 4,830,013.

Maxwell et al U.S. Pat. No. 5,057,278 discloses a calibration system in which sterile calibration liquid is equilibrated with the gas of interest and then pumped through the flow-through passage of the sensor cassette to be calibrated. Although this calibration system has many applications, it is particularly desirable for use with flow-through housings having a relatively small cross-sectional area.

In order to speed up the calibration process, it is desirable to reduce the time required for equilibration of the gas in the liquid. One way to accomplish this in a laboratory setting is to inject the gas through a porous, fritted stone into the liquid. This is accomplished in the laboratory by attaching a fritted stone to the end of a gas supply tube so that gas exiting from the tube must pass through the fritted stone. The gas supply tube with the fritted stone attached is then placed into a beaker containing the liquid. The gas then flows from the gas supply tube through the fritted stone into the liquid, and this does reduce somewhat the time required for equilibration. However, the fritted stone is relatively expensive and is not as efficient as desired in reducing equilibration time. Also, fritted stone is not suited for medical applications because of the possibility that it could introduce particulates into the liquid.

Calibration systems may employ tubing or other conduit means which are permeable to a component of air and/or the gas which is to be mixed with the calibration liquid. This permeability creates a possibility of air entering the calibration system or of the gas escaping from the system. In addition there is a possibility of mass transfer between various system components and the calibration liquid or between such systems components and the gas. These can be troublesome when it is necessary to accurately control the partial pressures of the gas of interest in the liquid.

SUMMARY OF THE INVENTION

An important feature of the present invention is substantially reducing the equilibration time to thereby materially shorten the time required for calibrating of the sensor cassette. Another important feature of this invention is the provision of a barrier on certain portions of the system to reduce permeability and/or mass transfer.

This invention is applicable, for example, to a calibration system comprising a sensor cassette which includes at least one sensor to be calibrated and with the sensor being responsive to a characteristic of a gas. The system also includes a housing have a liquid passage including a chamber. The housing is coupled to the sensor cassette to place the liquid passage in fluid communication with the sensor cassette. There is a sterile calibration liquid in the housing, and the housing has a gas injection passage through which a gas can be injected into the liquid passage to mix with the calibration liquid. Means, such as a gas vent on the housing, vents the gas from the housing.

To reduce equilibration time, porous media is positioned in the chamber so that the gas and calibration liquid can pass through the porous media to assist in mixing of the gas and the calibration liquid. This can be contrasted with the laboratory system described above in which a fritted stone was immersed in the liquid and only the gas was directed through the fritted stone. The passage of both the liquid and gas through the porous media causes turbulence that facilitates more efficient and quicker mixing of the gas into the liquid. In addition, the gas bubbles are broken up into finely dispersed bubbles as they strike the solid portions of the porous media, and this also provides more efficient and quicker mixing of the gas into the liquid.

Although the porous media can be of different types, it preferably includes an open cell polymeric foam. The polymeric foam is much less expensive than the fritted stone and can be provided in a porous structure which more efficiently mixes the liquid and gas.

Preferably, the foam has from about 3 to about 45 pores per inch (ppi) and at least about 20 percent open volume. In discussing open cell foam, it is understood that the term pores per inch or ppi refers to pores per lineal inch. Over about 45 pores per inch, the gas and liquid tend to take separate relatively straight paths through the foam and do not mix as quickly or efficiently as desired. Below about 3 pores per inch, there is a risk that there will be insufficient structure in the porous media to cause the desired turbulence. Under about 20 percent open volume, there is an increased tendency for the gas and liquid to form separate streams as they flow through the foam and therefore not mix as thoroughly as desired. There is no upper limit on the percent open volume except that there must be sufficient structure to provide adequate strength. For improved results, the porous media has from about 3 to about 7 pores per inch and at least about 85 percent open volume with 96 percent open volume being considered optimum.

The polymeric material of the porous media should be biocompatible and may be a polyester-polyurethane foam. To reduce any mass transfer between the foam and the calibration liquid and between the foam and the gas, the foam is preferably coated with an impermeable barrier. The mass transfer may be the transfer of a liquid, gas and/or solid. Although various different materials can be used for the barrier, very useful barrier materials are those selected from the polyxylylenes and mixtures thereof. A particularly useful polyxylylene is that sold under the trademark Parylene C and available from Viking Technology, Inc. of San Jose, Calif.

The porous media can also be located to enhance its performance. In a preferred construction, liquid and gas streams are brought together upstream of the porous media and then passed through the porous media. This can be accomplished, for example, when the housing has a liquid inlet and a liquid outlet coupled to the sensor cassette, and the liquid passage includes an inlet section leading from the liquid inlet to a junction at the chamber. The gas injection passage leads to a location in the inlet section of the liquid passage for injecting gas into the inlet section of the liquid passage at such location. The outlet is located to receive liquid that has passed from the inlet section of the liquid passage through the porous media.

Preferably the porous media is in the chamber adjacent the juncture of the liquid inlet and the chamber. More specifically, the housing includes a divider which divides the chamber into a sparging chamber section and a settling chamber section and the porous media is in the sparging chamber section.

The invention is also applicable to a calibration system which includes a pump in the housing for pumping liquid through the liquid passage and with the pump having a liquid path which forms a portion of the inlet section of the liquid passage. In this event, the gas injection passage and the inlet section of the liquid passage preferably meet at a location downstream of the pump and upstream of the sparging chamber.

Conduit means preferably couple the liquid inlet and liquid outlet of the housing to the sensor cassette. In at least some instances, a least one of the liquid passage and the conduit means includes a permeable portion which is at least somewhat permeable to the gas of interest and/or a component of air such as oxygen. This invention provides a barrier on such permeable portion which is less permeable than the permeable portion to such one of the gas and such component of air.

The obvious solution to this problem is to employ materials which are not permeable to either the gas or any component of air. However, other considerations may require that materials permeable to at least one of these gases must be used. For example, when a peristaltic pump is employed, a radially compressible tube is used as part of the pump. The tube, which must also be biocompatible, is preferably constructed of silicone which is permeable to oxygen and carbon dioxide. However, by coating the silicone tube with a barrier, its permeability to these gases is substantially reduced.

Another example is that the conduit means which couples the housing to the sensor cassette may include a first relatively soft and deformable section coupled to the housing and a second section which is less soft and less deformable than the first section coupled to the first section and to the sensor cassette. The first section must be sharply bent when packaged for shipping and storage and also must be biocompatible. This requires the use of a material, such as silicone, and silicone is permeable to both oxygen and carbon dioxide.

The barrier for the permeable portions may be the same barrier as that described above for use with the foam. This barrier, in addition to making the permeable portions less permeable or impermeable to the gases of interest, also reduces any mass transfer between the permeable portions and the calibration liquid and between the permeable portions and the gas.

Another feature of this invention is the use of a porous media in the chamber of the housing intermediate the porous media used for gas and liquid mixing and the gas vent. This porous media reduces the likelihood of liquid passing through the gas vent by breaking up bubbles and retaining the liquid component of the bubble. The preferred porous media is the same as that described above for the porous media used for mixing except that it preferably has about 3 to about 10 pores per inch and at least about 80 percent open volume. Below about 3 pores per inch, there is danger that there will be insufficient structure in the porous media to cause the desired break up of the bubbles. Above about 10 pores per inch, the surface tension may be sufficient to produce bubbles which escape through the gas vent.

Below 80 percent open volume, there is an increased likelihood that the liquid component of the bubbles will collect on the porous media in such a way that the pressure of the gas will pump or blow some of this collected liquid out through the gas vent. There is theoretically no upper limit on the percent open volume except that sufficient structure is required to support the porous media.

The invention, together with additional features and advantages thereof may best be understood by reference to the following description taken in connection with the accompanying illustrative drawings.

BRIEF DESCRIPTION OF THE DRAWINGS

FIG. 1 is a partially schematic illustration of a calibration system constructed in accordance with the teachings of this invention with the sensor cassette and portions of the housing being shown in cross section.

FIG. 2 is an enlarged sectional view taken generally along line 2—2 of FIG. 1.

FIG. 3 is an enlarged sectional view taken generally along line 3—3 of FIG. 1.

FIG. 4 is an enlarged fragmentary sectional view taken generally along line 4—4 of FIG. 1.

FIG. 5 is an enlarged fragmentary sectional view taken generally along line 5—5 of FIG. 1.

DESCRIPTION OF THE PREFERRED EMBODIMENT

FIG. 1 shows a sterile-loop calibration system 11 which generally comprises a sensor cassette 13, a calibration housing 15, sterile calibration liquid 16 and conduit means including a first conduit section 17, a second conduit section 19 coupled to the first conduit section 17 and to the sensor cassette 13 and a third conduit section 21 coupled to the other end of the housing 15 and the sensor cassette 13. The system 11 is disposable and designed for use with a known calibration instrument for calibrating the sensor cassette 13.

Although the sensor cassette 13 may be of various different constructions, in the embodiment illustrated, it is of the type shown in Gehrich et al U S. Pat. No. 4,989,606 entitled Intravascular Blood Gas Sensing System, which is incorporated by reference herein. Briefly, however the sensor cassette 13 includes a flowthrough passage 23 having first and second ends in the form tube fittings 25 and 27 which are joined to the conduit sections 21 and 19, respectively. Sensors 29, 31 and 33 which are to be calibrated are carried by the sensor cassette 13 in communication with the flow-through passage 23. The sensors 29, 31 and 33 may be, for example, for sensing carbon dioxide, pH and oxygen, respectively, and each of these sensors is covered by a semi-permeable membrane which is permeable to the constituent of interest as described in Gehrich et al U.S. Pat. No. 4,989,606 referred to above. The flow-through passage 23 has a very small cross sectional area and may be, for example, rectangular and have dimensions of about 0.015 inch by 0.164 inch.

Although the calibration housing 15 may be of various different constructions, the housing 15 illustrated is preferred. Except as shown or described herein, the calibration housing 15 may be identical to the calibration housing shown in Maxwell et al U.S. Pat. No. 5,057,278 and this patent is incorporated by reference herein.

The calibration housing 15 has an inlet 37, an outlet 39 and a liquid passage 41 extending through the housing from the inlet to the outlet. The liquid passage 41 includes a chamber 43 which is divided by a weir or dividing wall into a sparging chamber section 47 and settling chamber section 49. The flow-through passage 23, the conduit sections 17, 19 and 21, and the liquid passage 41 form a sterile loop which provides an endless loop in which the sterile calibration liquid 16 can be circulated.

The housing 15 has a gas injection passage 51 (FIG. 3) leading from a gas injection port 52 to a location in the liquid passage 41 for injecting gas into the liquid passage and means in the form of a threaded closure cap 53 (FIGS. 2 and 3) for closing the gas-injection port. The housing 15 also includes a gas vent 55 (FIGS. 1 and 4) which in this embodiment, includes a restricted orifice 56 having, for example, a diameter of about 1/16 inch. The gas vent 55 leads from the settling chamber section 49 to the exterior of the housing. The gas vent 55 may be completely closed by a closure cap 57 (FIGS. 1 and 4).

Although various constructions are possible, as shown in FIG. 3, the housing 15 includes a housing section 61 of multiple molded plastic components, such as a base 63, a cover 65 and a top section 67. At least the cover 65 and the top section 67 are preferably transparent. The base 63, the cover 65 and the top section 67 may be suitably coupled together as with an adhesive.

As shown in FIG. 1, the inlet 37 leads to an inlet passage section 69 of the liquid passage 41. A radially compressible tube 71 (FIGS. 1 and 2) communicates with the inlet passage section 69 through an aperture or opening 73 in the cover section 65 and with a chamber inlet section 75 (FIG. 2) through an aperture or opening 77 which also is in the cover 65. The chamber inlet section 75 leads to the sparging chamber section 47 as shown in FIG. 1.

The gas injection passage 51 (FIG. 3) is defined in part by an externally threaded tube 79 affixed to the top section 67. A gas-sterilizing filter 81 is supported on the cover 65 and retained in place by a spider section 82 of the top section 67. The gas-sterilizing filter 81 may be, for example, a 0.2 micron pore filter which is capable of sterilizing gas which passes through it due to the small pore size. Accordingly, with the cap 53 removed, a non-sterile gas can be introduced to the injection port 52 whereby it will pass through the filter 81, an aperture 83 in the cover 65, and a passage section 85 of the gas injection passage between the base 63 and the cover 65 to the chamber inlet section 75 as shown in FIGS. 1 and 3. The chamber inlet section 75 forms a right angle (FIG. 1), and the passage section 85 enters the apex of the right angle to form a "T" 84. Thus, the gas is injected into the liquid at a location where the direction of flow of the liquid is changing. For example, the gas injected into the gas injection passage 51 may comprise $CO_2$, $O_2$ and an inert gas, such as nitrogen.

With this construction, the sterile calibration liquid 16 and the gas therein, are introduced together into the sparging chamber section 47. The "T" 84 provides a premixing of the gas and liquid. As shown in FIG. 1 the base 63 preferably has a baffle 86 adjacent the weir 45 and above the location of junction where the chamber inlet section 75 opens into the sparging chamber section 47 for the purpose of breaking up larger bubbles that may exist in the liquid. A baffle 89 (FIG. 1) is provided adjacent the vent 55.

Although various constructions are possible, in the form shown in FIG. 4, a recess 91 in the cover 65 receives an externally threaded tube 93 which is affixed to the cover. The cap 57 is threadedly attached to the tube 93.

As shown in FIG. 1, the liquid passage 41 also includes an outlet passage section 95 leading from the settling chamber section 49 to the outlet 39. The housing 15 has a temperature sensing location which, in this embodiment, is in the form of a temperature well 97 adapted to receive a temperature probe in heat exchange relationship with the outlet passage section 95 as shown in FIG. 3. Although various constructions are possible, the outlet passage section 95 may communicate with the settling chamber section 49 through an aperture 99 as shown in FIG. 1. The aperture 99 is positioned to force flow to occur around the temperature well 97.

In order to move the calibration liquid 16 through the sterile loop, it is necessary to provide a pump to force the calibration liquid through the sterile loop 50. The pump is peristaltic and can be driven by an external rotary input or rotary driving element (not shown) which is part of the calibration apparatus 21. The pump components in the housing 15 include a curved wall surface 103 (FIG. 2, the compressible tube 71 and a tube compressor 105. The opposite ends of the tube 71 form an inlet and an outlet, respectively, for the pump.

More particularly, the wall surface 103 in this embodiment is cylindrical and constitutes the inner surface of a cylindrical boss 107, portions of which are formed integrally with the cover 65 and the top section 67. The tube compressor 105 is surrounded by the wall surface 103, and the tube 71 is wrapped in a circumferential direction about one time around the tube compressor and lies between the tube compressor and the wall surface 103.

The cover 65 and the top section 67 have flanges 109 and 111, respectively, which provide retaining surfaces for restraining the tube compressor 105 against axial movement relative to the wall surface 103. Because there is a radial clearance between the tube compressor 105 and the wall surface 103 and because the flanges 109 and 111 do not restrain the tube compressor against radial movement, the tube compressor is mounted on the housing for free radial movement relative to the wall surface 103 and the boss 107. In other words, the tube compressor 105 can be moved radially in any direction from the centered or neutral position shown in FIG. 2 with the only consequence being the squeezing of the compressible tube 71. With this construction, the tube compressor 105 can be caused to roll along the tube 71 to squeeze the tube in a zone which moves along the tube to thereby pump fluid in the tube. In the neutral position, the tube 71 is not squeezed.

The tube compressor 105 is generally cylindrical and tubular and has an outwardly opening cavity 113 having a mouth 115 which is flared radially outwardly to receive the rotary input (not shown). Thus, the cavity 113 provides means on the tube compressor 105 for use in releasably drivingly coupling the tube compressor to the external rotary element whereby the tube compressor can be rolled along the tube 71 to pump fluid in the tube.

To prevent leakage of the sterile calibration fluid 16, the opposite ends of the tube 71 are sealed to the confronting portions of the cover 65. Although this can be accomplished in different ways, as shown in FIG. 2, the opposite ends of the tube 71 have integral flanges 117 and 119 which are squeezed between a clamp ring 121 and the cover 65.

The housing 15 differs from the housing shown in Maxwell et al U.S. Pat. No. 5,057,278 in the provision of porous media 131 (FIG. 1) in the sparging chamber section 47. In this embodiment, the porous media 131 is an open cell polyester-polyurethane having from about 3 to about 7 pores per inch with a 96 percent open volume. The porous media 131 preferably fills the entire thickness dimension of the sparging chamber section 47 between the base 63 and the cover 65 as shown in FIG. 5 and the entire width dimension between the weir 45 and an opposite wall 132 of the chamber 43 to assure that the gas and liquid can not avoid passing through the porous media. In addition, to provide adequate time for mixing, the porous media 131 is preferably elongated so that it fills substantially the entire length of the sparging chamber section from just above the baffle 36 to a location substantially at the free end of the weir 45.

The calibration liquid 16 and the gas enter the sparging chamber section 47 together from the inlet section 75 at a juncture below the baffle 86. Although the porous media 131 could extend all the way to the juncture where the inlet section 75 opens into the sparging chamber section 47, in the illustrated embodiment, there is a gap 133 between the end of the inlet section 75 and a lower face 134 of the porous media 131.

The porous media 131 causes turbulence in the liquid that facilitates more efficient and quicker mixing of the gas into the liquid. In addition, the porous media 131 breaks up gas bubbles into finely dispersed bubbles as they strike the solid portion of the porous media, and this also facilities more efficient and quicker mixing of the gas into the liquid. In general, the porous media 131 increases the surface area of the gas exposed to the liquid, and this technique improves mixing as both the liquid and gas move through the porous media.

The housing 15 also differs from that disclosed in the Maxwell et al patent in providing porous media 135 (FIG. 1) in the settling chamber section 49 intermediate the porous media 131 and the gas vent 55 for reducing the likelihood of liquid passing through the gas vent. More specifically, the porous media 135 breaks up and collapses any bubbles attempting to exit through the gas vent 55 thereby minimizing liquid loss during calibration. In this embodiment, the porous media 135 is a polyester-polyurethane foam having about 3 to about 10 pores per inch and at least about 80 percent open volume. The porous media 135 is sized and located to so that all gas passing through the gas vent 55 must first pass through the porous media 135. Thus, the porous media 135 fills the entire thickness dimension of the settling chamber section 49 between the base 63 and the cover 65 as shown in FIG. 4. In addition, the entire width dimension between the baffle 89 and an outer wall 137 of the housing 15 is filled with the porous media 135. The porous media 135 has sufficient dimensions to allow ample opportunity for the destruction of bubbles attempting to pass through it.

With this construction, substantial mixing of the liquid and gas occurs in the sparging chamber section 47 and this mixed solution flows over the free end of the weir 45 and falls into the settling chamber section 49. In the settling chamber section 49, any remaining gas bubbles are given another opportunity to rise to the top and be vented through the vent 55. As indicated above the porous media 135 breaks up and collapses any bubbles attempting to exit through the gas vent 55.

In this embodiment, all the surfaces of the porous media 135 which come into contact with either the liquid or the gas are coated with a barrier to reduce mass transfer between the porous media and the liquid and between the porous media and the gas. In this particular embodiment, the barrier is Parylene C. The Parylene C can be applied to the porous media 135 utilizing, for example, vacuum deposition techniques.

In order that the tube 71 can be compressed to provide peristaltic pumping action in a sterile loop and so that the flanges 117 and 119, which are integral with the tube 71, can provide compressible seals, the tube 71 is constructed of a relatively soft, deformable and biocompatible material. The preferred material is silicone. However, silicone is permeable to oxygen and carbon dioxide. The gas which is mixed with the calibration liquid 16 includes oxygen and/or carbon dioxide because these are the gases, the partial pressures of which it is desired to control in the calibration liquid so that the sensors 29, 31 and 33 can be calibrated.

In addition, the conduit section 17 is also constructed of silicone. This enables the conduit section 17 to be bent sharply in packaging without forming a permanent kink in the conduit section when the system 11 is being used. Accordingly, the conduit section 17 is also constructed of silicone and is likewise permeable to oxygen and carbon dioxide.

This invention is further distinguished from the system disclosed is Maxwell et al U.S. Pat. No. 5,057,278 in that a barrier is provided on the gas permeable portions of the system 11 with such barrier being less permeable to the gases of interest than the permeable portion. In the illustrated embodiment, the tube 71 and the conduit section 17 are coated with a Parylene C barrier. The barrier is preferably applied to both the internal and external surfaces of the tube 71 and the conduit section 17 using, for example, a vacuum deposition process. The barrier reduces the rate at which the gases, notably oxygen and carbon dioxide, are able to diffuse through the conduit section 17 and the tube 71. The barrier also reduces the rate at which oxygen from the air can diffuse through the conduit section 17 and the tube 71 into the calibration liquid. In addition, the barrier reduces any mass transfer between the system components, i.e. the conduit section 17 and the tube 71 and the calibration liquid and between such system components and the gas. This increases the accuracy of the calibration process.

The system 11 can be used, for example, as described in Maxwell et al U.S. Pat. No. 5,057,278 to calibrate the sensor cassette 13. Briefly, when the system 11 is used to calibrate the sensors 29, 31 and 33 of the sensor cassette 13, a first calibration gas having known partial pressures of oxygen and $CO_2$, such as 60 millimeters of $CO_2$ and 100 millimeters of oxygen, is introduced through the port 52 while the pump is operated to circulate the calibration liquid 16 through the sterile loop defined by the housing 15, the sensor cassette 13 and the conduit sections 17, 19 and 21. The sensors 29 and 31 detect the partial pressure of the carbon dioxide and oxygen in the calibration liquid 16. During this time the porous media 131 and 135 functions as described above. When the calibration liquid 16 has the desired partial pressures of these two gases, an instrument or monitor (not shown) is used to establish one calibration point for the sensors. Thereafter, a second calibration gas having different levels of oxygen and carbon dioxide are introduced into the calibration liquid 16. For example, the second calibration gas may have a partial pressure of $CO_2$ of 20 millimeters and a partial pressure of oxygen of 40 millimeters. Following equilibration, a second calibration point is established in accordance with conventional techniques. With the partial pressures given in the above examples, the barrier acts to keep oxygen from the atmosphere out of the system 11 and to keep the carbon dioxide in the calibration liquid 16 and to reduce mass transfer as described above.

Although an exemplary embodiment of the invention has been shown and described, many changes, modifications and substitutions may be made by one having ordinary skill in the art without necessarily departing from the spirit and scope of this invention.

We claim:

1. A calibration system comprising:
   at least one sensor to be calibrated, said sensor being responsive to a characteristic of a gas;
   a housing having a liquid passage including a chamber, said housing being coupled to the sensor to place the liquid passage in fluid communication with the sensor;
   a sterile liquid in said liquid passage;
   said housing having a gas injection passage through which a gas can be injected into the liquid passage to mix with the liquid;
   means for venting the gas from the housing;
   porous medium comprising an open cell foam positioned down stream from said gas injection passage and in said chamber so that the gas and liquid can pass through the open cell foam to assist in mixing of the gas and the liquid, said open cell foam having from about 3 to about 7 pores per inch and at least about 85 percent open volume; and
   a barrier coated on said open cell foam to reduce any mass transfer between the open cell foam and the liquid and between the open cell foam and the gas.

2. A calibration system as defined in claim 1 wherein the open cell foam is a polyester-polyurethane foam.

3. A calibration system as defined in claim 1 wherein the barrier comprises polyxylylene.

4. A calibration system as defined in claim 1 wherein the open cell foam has about 96 percent open volume.

5. A calibration system as defined in claim 1 wherein the barrier comprises Parylene C.

6. A calibration system as defined in claim 1 wherein the housing includes a divider which divides the chamber into a sparging chamber section and a settling chamber section, said sparging chamber section being upstream from said settling chamber section, and wherein said porous medium is in the sparging chamber section.

7. A calibration system as defined in claim 6 wherein the porous media is in said sparging chamber section.

8. A calibration system as defined in claim 1 wherein the housing has a liquid inlet and a liquid outlet coupled to the sensor, said liquid passage includes an inlet section leading from the liquid inlet to a junction at the chamber, the gas injection passage leads to a location where the gas injection passage and the liquid passage meet for injecting gas into the inlet section of the liquid passage at said location and said outlet is located to receive liquid that has passed from the inlet section of the liquid passage through the porous media.

9. A calibration system as defined in claim 8 wherein the housing includes a divider which divides the chamber into a sparging chamber section and a settling chamber section, said sparging chamber section being upstream from said settling chamber section, said junction and said porous medium being in the sparging chamber section.

10. A calibration system as defined in claim 1 wherein at least a portion of the liquid passage is coated with a barrier which renders the liquid passage less permeable to the gas, a component of air, or both.

11. A calibration system as defined in claim 10 wherein the barrier coated on the portion of the liquid passage comprises polyxylylene.

12. A calibration system as defined in claim 10, wherein the barrier coated on the portion of the liquid passage comprises Parylene C.

13. A calibration system as defined in claim 1 wherein the venting means includes a gas vent on the housing leading from said chamber and the calibration system includes second porous media comprising a second open cell foam in the chamber intermediate the first mentioned open cell foam and the gas vent for reducing the likelihood of liquid passing through the gas vent.

14. A calibration system as defined in claim 7 wherein the second open cell foam has from about 3 to about 7 pores per inch and at least about 85 percent open volume.

15. A calibration system as defined in claim 13 further comprising a second barrier coated on the second open cell foam to reduce any mass transfer between the second open cell foam and the liquid and between the second open cell foam and the gas.

16. A calibration system as defined in claim 15 wherein the second barrier comprises polyxylylene.

17. A calibration system as defined in claim 15 wherein the second barrier comprises Parylene C.

18. A calibration system as defined in claim 15 wherein the least a portion of the liquid passage is coated with a barrier which renders the liquid passage less permeable to the gas, a component of air, or both.

19. A calibration system as defined in claim 18 wherein the barriers coated on both the first and second open cell foams comprise polyxylylene and wherein the barrier coated on the portion of the liquid passage comprises polyxylylene.

20. A calibration system as defined in claim 19 wherein said portion of the liquid passage is formed of a material comprising silicone.

21. A method of calibrating a sensor of the type having a flow-through passage, comprising the steps of:
   pumping a sterile liquid through an endless path which includes the flow-through passage;

injecting a sterile gas into the path to create a partial pressure of the gas in the path;

mixing the gas with the sterile liquid in the endless path to control the partial pressure of at least a component of said gas in the sterile liquid;

said step of mixing including passing the gas and liquid through an open cell foam, the open cell foam having from about 3 to about 7 pores per inch and at least about 85 percent open volume, the open cell foam further comprising a barrier coated thereon to reduce any mass transfer between the open cell foam and the liquid and between the open cell foam and the gas;

venting at least some of the gas from the endless path; and exposing the sensor to the sterile liquid having the controlled partial pressure of said component of said gas whereby the sensor can be calibrated.

22. A method as defined in claim 21 wherein the barrier comprises polyxylylene.

23. A method as defined in claim 21 wherein the barrier comprises Parylene C.

24. A method as defined in claim 21 wherein at least a portion of the endless path is coated with a barrier which renders the endless path less permeable to the gas, a component of air, or both.

25. A method as defined in claim 21 wherein said step of venting includes passing the gas through a second open cell foam subsequent to said step of mixing.

26. A method as defined in claim 25 wherein the second open cell foam is coated with a barrier to reduce any mass transfer between the second open cell and the liquid and between the second open cell foam and the gas.

27. A method as defined in claim 26 wherein the barrier coated on the second open cell foam comprises polyxylylene.

28. A method as defined in claim 26 wherein at least a portion of the endless path is coated with a barrier which renders the endless path less permeable to the gas, a component of air, or both.

29. A method as defined in claim 28 wherein the barriers coated on both open cell foams comprise polyxylylene and wherein the barrier coated on the portion of the endless path comprises polyxylylene.

* * * * *

UNITED STATES PATENT AND TRADEMARK OFFICE
CERTIFICATE OF CORRECTION

PATENT NO. : 5,278,072

DATED : January 11, 1994

INVENTOR(S) : Roxanne E. Wall et al.

It is certified that error appears in the above-indentified patent and that said Letters Patent is hereby corrected as shown below:

Col. 9, line 47, claim 1, line 13, "medium" should be --media--.

Col. 10, line 2, claim 6, line 6, "medium" should be --media--.

Col. 10, line 20, claim 9, line 6, "medium" should be --media--.

Col. 10, line 29, claim 12, line 1, after "10" delete the comma.

Col. 10, line 39, claim 14, line 1, "7" should be --13--.

Col. 10, line 54, claim 18, line 2, delete the first occurrence of "the" and substitute therefor --at--.

Col. 12, line 10, claim 26, line 3, after "cell" insert --foam--.

Signed and Sealed this

Fifth Day of July, 1994

Attest:

BRUCE LEHMAN

Attesting Officer     Commissioner of Patents and Trademarks